United States Patent [19]

Zink

[11] Patent Number: 4,525,588
[45] Date of Patent: Jun. 25, 1985

[54] CHROMOGENIC NAPHTHOLACTAMS

[75] Inventor: Rudolf Zink, Therwil, Switzerland

[73] Assignee: Ciba Geigy Corporation, Ardsley, N.Y.

[21] Appl. No.: 502,039

[22] Filed: Jun. 7, 1983

[30] Foreign Application Priority Data

Jun. 14, 1982 [CH] Switzerland .......................... 3666/82

[51] Int. Cl.³ .................. C07D 239/72; C07D 265/12
[52] U.S. Cl. .................................. 544/89; 260/243.3; 430/138; 544/58.6; 544/70; 544/95; 544/105; 544/230; 544/245; 544/248
[58] Field of Search ................... 544/89, 95, 245, 248, 544/105, 58.6, 70, 230; 260/243.3

[56] References Cited

U.S. PATENT DOCUMENTS 3,959,270  5/1976  Fauran et al. ................... 544/89 X Primary Examiner—Richard L. Raymond
Attorney, Agent, or Firm—Edward McC. Roberts; Kevin T. Mansfield

[57] ABSTRACT

The invention relates to chromogenic naphtholactams of the general formula

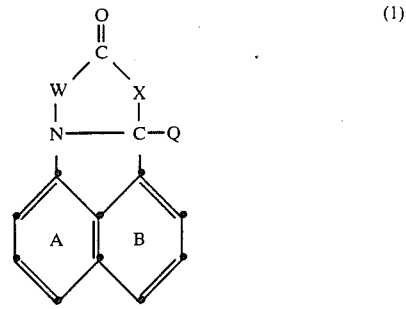

wherein
Q is the radical of a couplable compound,
X is oxygen or

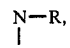

wherein R is hydrogen, lower alkyl or aryl, and
W is alkylene, cycloalkylene or a 6-membered isocyclic or heterocyclic aromatic radical which is unsubstituted or substituted or which may contain a fused benzene ring; and each of the rings A and B independently of the other are unsubstituted or substituted.

These compounds are particularly suitable for use as color formers in pressure-sensitive or heat-sensitive recording materials and, depending on the meaning of X and Q, give orange, red, violet and blue colorations.

10 Claims, No Drawings

CHROMOGENIC NAPHTHOLACTAMS

The present invention relates to chromogenic naphtholactams, to the preparation thereof, and to the use of these compounds as colour formers in pressure-sensitive or heat-sensitive recording materials.

The chromogenic naphtholactams of this invention have the general formula

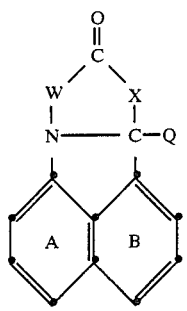

(1)

wherein
Q is the radical of a couplable compound,
X is oxygen or

wherein R is hydrogen, lower alkyl such as methyl, or aryl such as phenyl, and
W is alkylene, cycloalkylene or a 6-membered isocyclic or heterocyclic aromatic radical which is unsubstituted or substituted or which may contain a fused benzene ring; and each of the rings A and B independently of the other is unsubstituted or substituted.

Couplable compounds of which Q is a radical may be N-monosubstituted or N,N-disubstituted anilines or naphthylamines, N-unsubstituted or N-substituted indoles, indolines, carbazoles, tetrahydrocarbazoles, dihydroquinolines or tetrahydroquinolines, dibenzylimides or benzomorpholines; phenol ethers or naphthol ethers, preferably lower alkyl ethers; diphenyl ethers and also phenylpyrazolines.

The monocyclic or polycyclic, carbocyclic or heterocyclic couplable compounds may also contain one or more ring substituents. Suitable C-substituents are e.g. halogens, hydroxyl, cyano, nitro, lower alkyl, lower alkoxy, lower alkoxycarbonyl, $C_1$-$C_8$-acyl, preferably lower alkanoyl, or phenyl, whilst N-substituents are preferably $C_1$-$C_{12}$-alkyl, $C_3$-$C_{12}$ alkenyl or benzyl, each of which may also be substituted by e.g. halogen, nitro, hydroxyl, lower alkyl, lower alkoxy or lower alkoxycarbonyl.

The bridge member X is preferably oxygen or, most preferably, —NH. X may also be with advantage

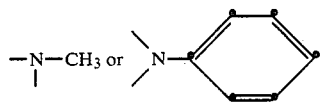

An alkylene radical W preferably contains 1 to 4 carbon atoms and may be straight chain or branched. W as cycloalkylene is preferably cyclohexylene.

An isocyclic aromatic radical W is preferably a benzene ring which is unsubstituted or substituted by halogen, methyl or methoxy. A 6-membered heterocyclic radical W is preferably a nitrogen-containing heterocyclic ring of aromatic character such as a pyridine or pyrazine ring. Both the carbocyclic and the heterocyclic ring may also contain a fused benzene ring and are therefore e.g. a naphthalene or a quinoline ring.

W is preferably phenylene or, most preferably, ethylene.

The rings A and B of the naphtholactam may contain non-ionic substituents or be unsubstituted. Examples of suitable substituents are: halogen, preferably chlorine or bromine; lower alkyl, lower alkoxy, N,N-di-lower alkylamino or N-lower alkyl-N-arylamino groups, e.g. methyl, ethyl, butyl, methoxy, ethoxy, dimethylamino, N-methyl-N-ethylamino or N-ethyl-N-phenylamino; acyl or acylamino radicals, preferably lower alkanoyl, lower alkanoylamino, lower alkoxycarbonyl, lower alkoxycarbonylamino, lower alkylated carbamoyl or ureido groups, e.g. acetyl, acetylamino, benzoylamino, ethoxycarbonylamino or N,N-dimethylaminocarbonylamino, sulfonyl or sulfamoyl radicals, preferably lower alkylsulfonyl, arylsulfonyl or N,N-di-lower alkylsulfamoyl radicals such as methylsulfonyl, phenylsulfonyl or N,N-dimethylsulfamoyl.

Lower alkyl and lower alkoxy normally denote groups or moieties of groups which contain 1 to 5, preferably 1 to 3, carbon atoms. Lower alkyl is e.g. methyl, ethyl, isopropyl, sec- and tert-butyl, and lower alkoxy is e.g. methoxy, ethoxy or isopropoxy.

Acyl is preferably formyl, lower alkanoyl, lower alkenoyl or benzoyl. Further acyl radicals may be lower alkylsulfonyl, e.g. methylsulfonyl or ethylsulfonyl, and phenylsulfonyl. Benzoyl and phenylsulfonyl may be substituted by halogen, methyl, methoxy or ethoxy.

Lower alkanoyl and lower alkenoyl relate to a carbon chain which contains not more than 5 carbon atoms, e.g. acetyl, propionyl, butyryl, acryloyl or crotonyl.

Halogen is e.g. flourine, bromine or, preferably, chlorine.

Useful chromogenic naphtholactams are those of the formula

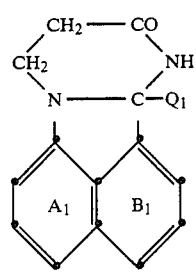

(2)

wherein $Q_1$ is a substituted phenyl radical of the formula a 3-indolyl radical of the formula

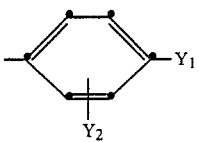

a 3-carbazolyl radical of the formula

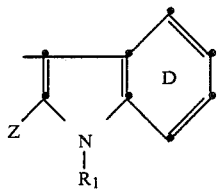

a 3-indolinyl radical of the formula

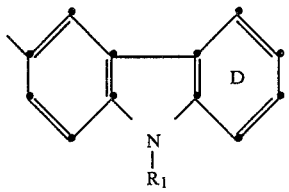

a tetrahydroquinolinyl radical of the formula

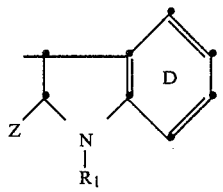

or

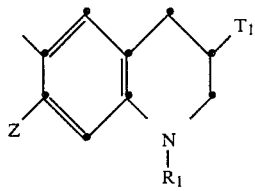

or a benzomorpholino radical of the formula

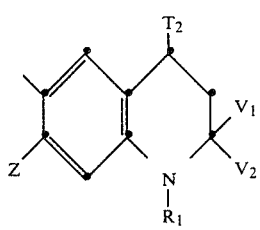

$Y_1$ is $-OZ_1$ or

$Y_2$ is hydrogen, halogen, nitro, lower alkyl or lower alkoxy,

Z is hydrogen, lower alkyl or phenyl, $Z_1$ and $Z_2$, each independently of the other, are hydrogen, $C_1$–$C_{12}$-alkyl which is unsubstituted or substituted by halogen, hydroxyl or lower alkoxy, or are cycloalkyl, phenyl, benzyl, or phenyl or benzyl each substituted by halogen, nitro, cyano, lower alkyl, lower alkoxy or lower alkoxycarbonyl or $Z_1$ and $Z_2$, together with the nitrogen atom to which they are attached, are a 5- or 6-membered saturated heterocyclic radical, $R_1$ is hydrogen, $C_1$–$C_{12}$ alkyl which is unsubstituted or substituted by halogen, hydroxyl or lower alkoxy, or is benzyl or benzyl which is substituted by halogen, nitro, lower alkyl or lower alkoxy, $T_1$ and $T_2$, each independently of the other, are hydrogen, halogen, hydroxy, lower alkyl or lower alkoxy, $V_1$ and $V_2$, each independently of the other, are hydrogen, lower alkyl, cycloalkyl or benzyl, or both taken together are alkylene; and the rings $A_1$, $B_1$ and D, each independently of one another, are unsubstituted or substituted by halogen, nitro, cyano, lower alkyl, lower alkoxy or lower alkoxycarbonyl.

Preferred naphtholactams of the formula (2) are those in which $Q_1$ is a substituted phenyl radical of the formula (2a) or a tetrahydroquinolinyl radial of the formula (2f). In formula (2a), $Y_1$ is preferably $-NZ_1Z_2$. $Y_2$ is preferably hydrogen, methyl, methoxy or ethoxy and is preferably in the m-position relative to the substituent $Y_1$.

The radicals $Z_1$ and $Z_2$ may differ from each other or they are preferably identical.

Alkyl groups $R_1$, $Z_1$ and $Z_2$ may be straight chain or branched. Examples of such alkyl groups are methyl, ethyl, n-propyl, isopropyl, n-butyl, sec-butyl, amyl, n-hexyl, 2-ethyl-hexyl, n-octyl, isooctyl or n-dodecyl.

$R_1$, $Z_1$ and $Z_2$ as substituted alkyl groups are in particular haloalkyl, hydroxyalkyl or alkoxyalkyl, each containing preferably a total of 2 to 4 carbon atoms, e.g. β-chloroethyl, β-hydroxyethyl, β-methoxyethyl or β-ethoxyethyl.

$V_1$, $V_2$, $Z_1$ and $Z_2$ as cycloalkyl may be cyclopentyl or, preferably, cyclohexyl.

Preferred substituents in the benzyl moiety of $R_1$, $Z_1$ and $Z_2$ and in the phenyl moiety of $Z_1$ and $Z_2$ are e.g. halogens, nitro, methyl or methoxy. Examples of such (2a) 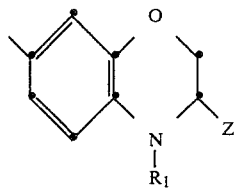

(2b)

(2c)

(2d)

(2e)

(2f)

(2g)

araliphatic and aromatic radicals are p-methylbenzyl, o- or p-chlorobenzyl, o- or p-nitrobenzyl, o- or p-tolyl, xylyl, o-, m- or p-chlorophenyl, o- or p-nitrophenyl, or o- or p-methoxyphenyl.

A heterocyclic radical represented by $Z_1$ and $Z_2$, together with the nitrogen atoms to they are attached, is e.g. pyrrolidino, piperidino, pipecolino, morpholino, thiomorpholino or piperazino, e.g. N-methylpiperazino.

$Z_1$ and $Z_2$ are preferably lower alkyl, benzyl or phenyl.

The N-substituent $R_1$ is preferably benzyl or $C_1$-$C_8$-alkyl, e.g. n-octyl, n-butyl or, most preferably, methyl or ethyl.

$T_1$ is preferably hydrogen, hydroxyl or chlorine, $T_2$ is preferably hydrogen, methyl or ethyl. Each of $V_1$ and $V_2$ is preferably lower alkyl and, most preferably, methyl.

Where $V_1$ and $V_2$ together are alkylene, they contain with advantage 4 or 5 carbon atoms and, together with the carbon atom to which they are attached, form a cyclopentane or cyclohexane ring. The rings $A_1$, $B_1$ and D are preferably unsubstituted or substituted by halogen or lower alkoxy, e.g. by chlorine or methoxy.

Particularly interesting naphtholactams are those of the formula

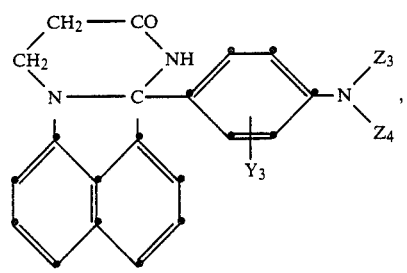  (3)

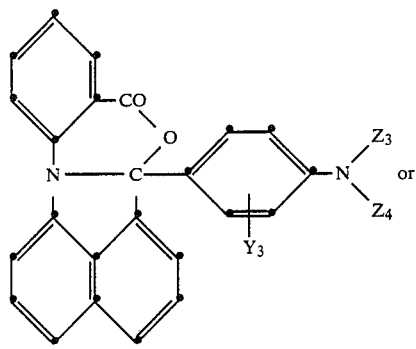  (4)

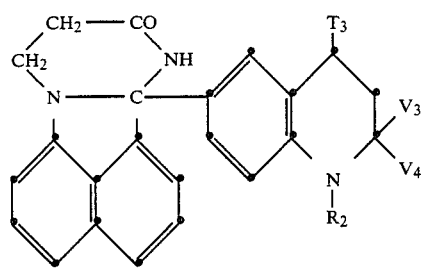  (5)

wherein $Z_3$ is lower alkyl, phenyl, lowr alkylphenyl, lower alkoxyphenyl or benzyl, $Z_4$ is lower alkyl, phenyl or benzyl, $Y_3$ is hydrogen, halogen, methyl, methoxy or ethoxy, $T_3$, $V_3$ and $V_4$, each independently of the other, are lower alkyl, preferably methyl or ethyl, and $R_2$ is $C_1$-$C_8$ alkyl or benzyl.

The naphtholactams of the formula (1), wherein X is —NH— and W is ethylene, are prepared by hydrolysing (saponifying) a cyanoethylated naphtholactam of the formula

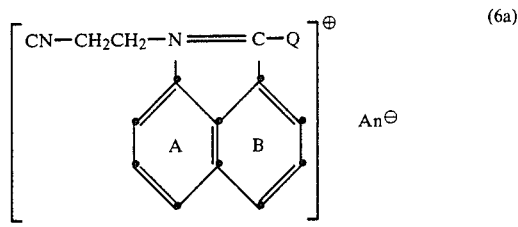  (6a)

or its carbinol base of the formula

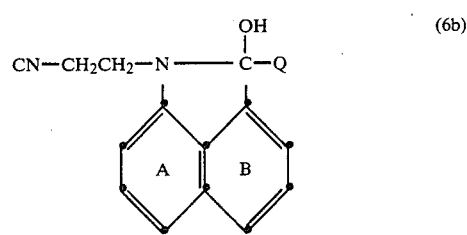  (6b)

in which formulae A, B and Q have the meanings assigned to them and $An^\ominus$ is an anion, in particular of a strong mineral acid, e.g. a halide, sulfate or perchlorate, or of an organic acid, e.g. a formate or acetate, or a complex anion, e.g. of a zinc chloride double salt, to give the corresponding carbamoylethyl compound, which is then cyclised to give the compound of formula (1).

The reaction is conveniently carried out in aqueous medium, using a dilute alkaline solution of an alkali metal alcoholate, e.g. sodium methanolate, or preferably an alkali metal hydroxide solution, e.g. sodium hydroxide or potassium hydroxide solution, for the amide formation and the cyclisation. The saponification of the nitrile group to the acid amide group can with advantage be carried out in sulfuric acid instead of in an alkali metal hydroxide solution.

The temperature for the amide formation normally depends on the saponifying agent and is conveniently in the range from 10° to 100° C., preferably from 20° to 45° C.

The starting materials of the formula (6a) can be prepared in a manner known per se. A preferred process comprises reacting an N-(2-cyanoethyl)-1,8-naphtholactam with a couplable compound Q-H, wherein Q has the given meaning, in the presence of a condensing agent such as an acid halide and optionally zinc oxide, in the temperature range from 20° to 120° C., in accordance with C.A. Vol. 94, 32181s.

Suitable acid halides are acid bromides or preferably acid chlorides, of phosphorous acid or sulfurous acid, of phosphoric acid, sulfuric acid, carbonic acid or oxalic acid. It is advantageous to use oxalyl chloride, oxalyl bromide, thionyl chloride, sulfuryl chloride, phosphorus trichloride, phosphorus tribromide or, preferably, phosgene or, most preferably, phosphoroxy trichloride.

Examples of couplable compounds which may be used as starting materials of the formula QH are: methoxybenzene, 1,3-dimethoxybenzene, 1-methyl-3-methoxybenzene, 1-phenyl-3,5,5-trimethylpyrazoline, 1-methoxynaphthalene, N-methylaniline, N-ethylaniline, N-ethyl-2-methylaniline, N-tolylaniline, N,N-dibenzylaniline, N-methyl-N-phenylamine, N-ethyl-N-phenylaniline, N-methyl-N-benzylaniline, N-ethyl-N-benzylaniline, N,N-diethylaniline, N,N-dimethylaniline, N-ethyl-1,2,3,4-tetrahydrocarbazole, 1-ethyl-3-hydroxy-7-methyl-1,2,3,4-tetrahydroquinoline, 1-ethyl-3-chloro-1,2,3,4-tetrahydroquinoline, 1-ethyl-2,2,4-trimethyl-1,2,3,4-tetrahydroquinoline, N-methylbenzomorpholine, N-ethyl-3-methylbenzomorpholine, 1-methyl-3-phenylbenzomorpholine, 1-ethylcarbazole, 1-n-butylcarbazole, 1-methylindole, 1-ethylindole, 1-methyl-2-phenylindole, 1,2-dimethylindole, 1-propyl-2-methylindole, 1-ethyl-2-methyl-5-methoxyindole, 1-butylindole, 1-pentyl-2-methylindole, 1-benzyl-2-methylindole, 1-octyl-2-methylindole, 1-dodecyl-2-methylindole, 1-methyl-7-ethylindole, 1-methyl-5-ethoxyindole, 1-methyl-5-chloroindole, 1-methyl-5-bromoindole, 1-methyl-7-chloroindole, 1-(2'-carboethoxy)ethyl-2-methylindole, 1-(2'-N-methylcarbamoyl)ethyl-2-methylindole, 1-allyl-2-methylindole or dibenzylimide.

The carbinol bases of the formula (6b) can be prepared in accordance with German Offenlegungsschrift No. 2 333 261.

A further process for obtaining the compounds of formula (1) comprises cyclising a naphtholactam of the formula

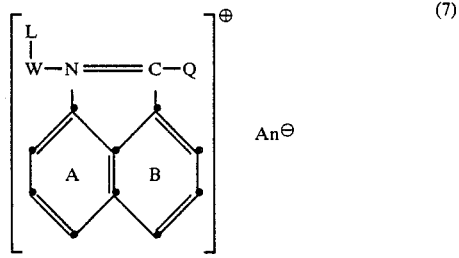

(7)

wherein L is —CONH—R or —COOR', wherein R' is hydrogen or lower alkyl, and A, B, Q, W, R and $An^\ominus$ have the given meanings, in aqueous-alkaline medium.

Depending on the meaning of W and L, the corresponding naphtholactams of the formula (7) are obtained by reacting a naphtholactam of the formula

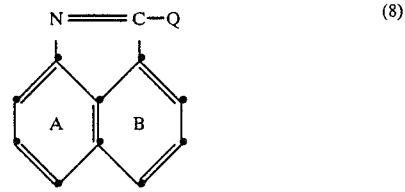

(8)

wherein A, B and Q have the given meanings, or a salt thereof, with a corresponding carboxylic acid, carboxylic acid lower alyl ester or carboxylic acid amide, which is unsubstituted or substituted by anionic removable groups, e.g. acrylic acid, methacrylic acid, methyl acrylate, acrylamide, haloacetic acid, β-halopropionic acid, 2-halobenzoic acid, haloacetamide, halo-N-lower alkyl acetamide, β-halopropionamide or β-halo-N-lower alkyl propionamide, preferably in the temperature range from 50° to 150° C.

The chromogenic naphtholactams of the formulae (1) to (5) are normally colourless or, at most, faintly coloured. When these colour formers are brought into contact with a preferably acid developer, e.g. an electron acceptor, they produce intense orange, red, violet or blue shades of excellent fastness to sublimation and light. They are therefore also very useful when mixed with one or more other known colour formers, for example 3,3-(bis-aminophenyl)phthalides, 3,3-(bis-indolyl)phthalides, 3-aminofluoranes, 2,6-diaminofluoranes, leucoauramines, spiropyranes, spirodipyranes, chromenoindoles, phenoxazines, phenothiazines, carbazolylmethanes or other triarylmethaneleuco dyes, to give blue, navy blue, grey or black colorations.

The naphtholactams of the formulae (1) to (5) exhibit both on phenolic substrates, and especially on activated clays an improved colour intensity and lightfastness. Depending on the meaning of X and Q they are suitable in particular as very rapidly, or preferably slowly, developing colour formers for use in a heat-sensitive or especially in a pressure-sensitive recording material which can also be a copying material.

A pressure-sensitive material consists, for example, of at least one pair of sheets which contain at least one colour former of the formulae (1) to (5) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, activated kaolin or any clay. Preferred developers are acidic organic compounds, for example unsubstituted or ring-substituted phenols, salicyclic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are zinc salicylates or the condensation products of p-substituted phenols with formaldehyde. These latter may also contain zinc.

The developers may also be used with other basically inert or almost inert pigments. Examples of such pigments are: talcum, titanium dioxide, zinc oxide, chalk, clays such as kaolin, as well as organic pigments, e.g. urea/formaldehyde or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomblike structures. The colour formers are preferably encapsulated in microcapsules, which as a rule can be ruptured by pressure.

When the capsules are ruptured by pressure, for example with a pencil, the colour former solution is transferred to an adjacent sheet which is coated with an electron acceptor and a coloured area is thus produced.

This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, naphthalene or triphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specification Nos. 989 264, 1 156 725, 1 301 052 and 1 335 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (5) can be used for the production of a wide variety of known kinds of pressure-sensitive copying material. The various systems differ substantially from one another in the arrangement of the capsules, of the colour reactants, i.e. the developers, and/or of the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (5) can also be employed as colour formers in a thermoreactive recording material. This recording material usually contains at least one carrier, one colour former, one electron acceptor and, optionally, also a binder. Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heatinduced marks The thermoreactive recording material can be composed such that the colour former is dispersed or dissolved in one binder layer and the developer is dissolved or dispersed in the binder in a second layer.

Another possibility consists in dispersing both the colour former and the developer in one layer. Be means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenyl, 4-phenylphenol, 4-hydroxydiphenyl ether, α-naphtol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl)valeric acid, 2,2'-methylene-bis-(4-phenylphenol), hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxylic acid, maleic acid, citric acid, citraconic acid or succinic acid.

Fusible, film-forming binders are preferably used for the manufacture of the thermoreactive recording material. These binders are normally water-soluble, whereas the naphtholactams and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, gelatin or starch.

If the colour former and the developer are in two separate layers, it is possible to use water-insoluble binders, i.e. binder which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stearates, phthalonitrile or other appropriate fusible products which induce the simultaneous melting of the colour former and the developer. Thermographic recording materials preferably contain waxes, e.g. carnauba wax, montan wax, paraffin wax or polyethylene wax.

The invention is illustrated by the following Examples, in which percentages are by weight, unless otherwise indicated.

EXAMPLE 1

14.8 g of an ammonium salt of the formula

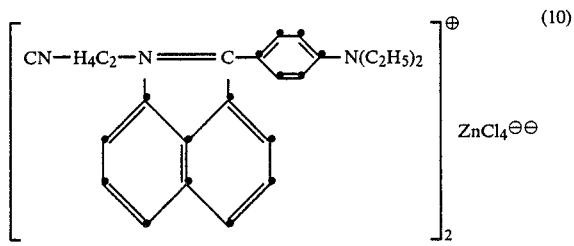

(10)

prepared according to C.A. Vol. 94, 32 181s, are added at 20°–25° C. to 36 g of 98% sulfuric acid and the mixture is stirred for 16 hours at the same temperature. The solution is poured into 300 g of ice/water and the dilute solution is then adjusted to pH 12 at 45° C. with 30% sodium hydroxide solution. The precipitate is isolated by filtration, washed with water until neutral and dried in vacuo at 75° C., affording 11.8 g of a compound of the formula

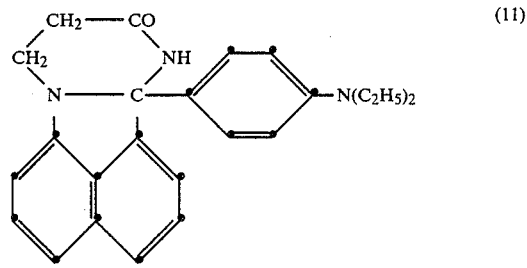

(11)

which melts at 222°–223° C. after recrystallisation from toluene. This colour former develops an intense and lightfast blue colour on acid clay.

In the same manner as described in this Example, the colour formers of the formula

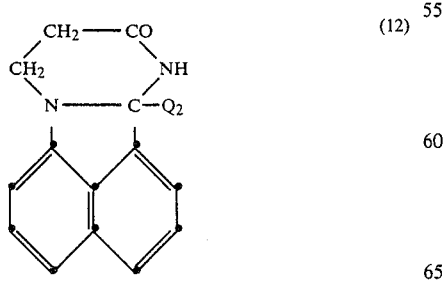

(12)

listed in the following table are obtained using the corresponding quaternary ammonium salt.

TABLE

| Example No. | Q₂ | mp./°C. | Colour on acid clay |
|---|---|---|---|
| 2 | 4-N(CH₃)₂, 3-OCH₃ phenyl | 260 | blue |
| 3 | 4-N(CH₂-phenyl)₂ phenyl | 126–128 | reddish blue |
| 4 | 4-N(CH₃)(CH₂-phenyl) phenyl | 179–180 | reddish blue |
| 5 | 4-N(CH₃)₂ phenyl | 265–266 | reddish blue |
| 6 | 1,2-dihydro-2,2,4-trimethyl-1-ethyl-quinolin-6-yl | 240 | blue |
| 7 | 1-ethyl-2,2-dimethyl-4-oxo-1,2,3,4-tetrahydroquinolin-6-yl | 264–265 | blue |
| 8 | 3,4-dimethoxyphenyl | 242–243 | orange |
| 9 | 1-methyl-2-phenyl-3-methyl-indol-3-yl | 280 | violet |
| 10 | 1-ethyl-2-methyl-indol-3-yl | 202–204 | reddish violet |
| 11 | 9,10-dihydro-9-methyl-acridin-... | 242–244 | blue |

EXAMPLE 12

5 g of the carbinol base of the formula

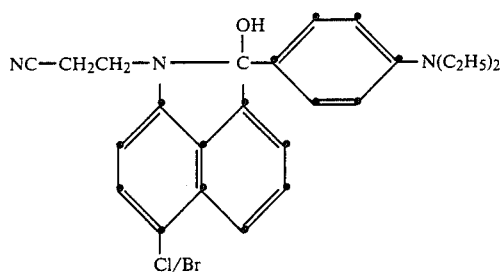

(13)

prepared according to German Offenlegungsschrift No. 2 333 261, are added at 20°–25° C. over 1 hour to 50 g of 98% sulfuric acid. The reaction mixture is then stirred first for 16 hours at 20°–25° C. and subsequently for 3 hours at 35°–40° C. The solution is poured into 300 g of ice/water and adjusted to pH 13 with 30% sodium hydroxide solution. The resultant suspension is stirred for 1 hour at 40° C., then the precipitate is isolated by filtration and dried. Recrystallisation of the crude product from chlorobenzene yields 2.6 g of a colourless compound of the formula

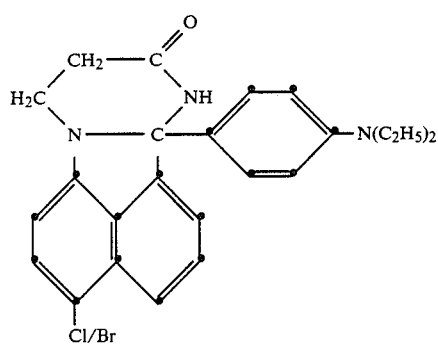

(14)

with a melting point of 203°–205° C.

This colour former develops a greenish blue colour of excellent lightfastness on acid clay.

EXAMPLE 13

33.8 g of 1,8-naphtholactam, 50 g of 2-bromobenzoic acid, 15 g of potassium carbonate, 1 g of copper powder and 1 g of potassium iodide are mixed and fused at 120° C. The melt is heated to 185° C. and kept at this temperature for 1 hour. After cooling to 110° C., 100 g of toluene are added to the melt and the toluene layer is then separated. The toluene solution is cooled, whereupon the product precipitates. The precipitate is isolated by filtration and dried, affording 44 g of a compound of the formula

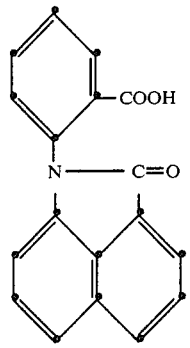

(15)

with a melting point of 236°–237° C. (with decompos.).

7.2 g of the above compound is condensed with 3.7 g of N,N-diethylaniline in accordance with C.A. Vol. 94, 32181s. The reaction solution is poured into water and the aqueous solution is adjusted to pH 12 with sodium hydroxide. The precipitated product is extracted at 80° C. with 100 g of toluene and recrystallised after cooling the toluene solution. The product is isolated by filtration and dried, affording 2.3 g of a compound of the formula

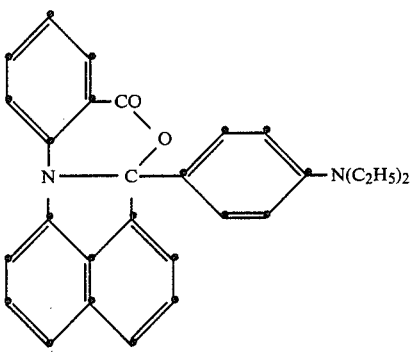

(16)

which melts at 190°–195° C. (decompos.). This compound develops rapidly an intense lightfast blue colour on acid clay.

EXAMPLE 14

Preparation of a pressure-sensitive copying paper.

A solution of 3 g of the naphtholactam obtained in Example 6 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or typewriter and an intense blue copy of excellent lightfastness develops immediately on the sheet coated with the developer.

EXAMPLE 15

1 g of the naphtholactam of Example 6 is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and coated on a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and an intense and lightfast blue copy develops immediately on the sheet coated with the colour former.

EXAMPLE 12

Preparation of a heat-sensitive recording material.

In a ball mill, 32 g of 4,4'-isopropylidenediphenol (bisphenol A), 3.8 g of the distearylamide of ethylenediamine, 38 g of kaolin, 20 g of an 88% hydrolysed polyvinyl alcohol and 500 ml of water are ground to particle size of about 5 μm. In a second ball mill, 6 g of the naphtholactam of the formula (11), 3 g of an 88% hydrolysed polyvinyl alcohol and 60 ml of water are ground to particle size of about 3 μm.

Both dispersions are mixed and coated on paper to a dry coating weight of 5.5 g/m². An intense blue colour of excellent fastness to light and sublimation is produced by contacting the paper with a heated ball-point pen.

EXAMPLE 13

In a ball-mill, 2.7 g of the naphtholactam of Example 6, 24 g of N-phenyl-N'-(1-hydroxy-2,2,2-trichloroethyl)-urea, 16 g of stearylamide, 59 g of an 88% hydrolysed polyvinyl alcohol and 58 ml of water are ground to a particle size of 2–5 μm. This suspension is coated on a sheet of paper to a dry coating weight of 5.5 g/m². An intense and lightfast blue colour is obtained by contacting the paper with a heated ball-point pen.

What is claimed is:

1. A chromogenic naphtholactam of the formula

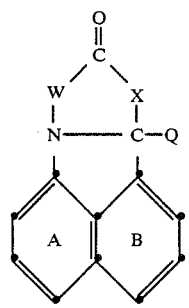

wherein
each of the rings A and B independently of the other is unsubstituted or substituted by halogen, lower alkyl, lower alkoxy, N,N-dilower alkylamino, N-lower alkyl-N-arylamino, acyl or acylamino,
X is oxygen or

wherein R is hydrogen, lower alkyl or aryl,
W is ethylene, cyclohexylene, or a benzene, naphthalene, pyridine, pyrazine or quinoline ring, or a benzene ring substituted by halogen, methyl or methoxy, and
Q is the radical of a couplable compound selected from the group consisting of a
N-monosubstituted or N,N-disubstituted aniline, a
N-monosubstituted or N,N-disubstituted naphthylamine, a
N-unsubstituted or N-substituted indole, indoline, carbazole, tetrahydrocarbazole, dihydroquinoline, tetrahydroquinoline, dibenzylimide and benzomorpholine, and
a phenol-lower alkyl ether,
a naphthol-lower alkyl ether,
a diphenylether and a phenylpyrazoline,
wherein such a radical of a couplable compound is C-unsubstituted or C-substituted by halogen, hydroxyl, cyano, nitro, lower alkyl, lower alkoxy, lower alkoxycarbonyl or $C_1-C_8$-acyl and wherein the N-substituent is $C_1-C_{12}$-alkyl, $C_3-C_{12}$-alkenyl or benzyl, each of which is unsubstituted or substituted by halogen, nitro, hydroxyl, lower alkyl, lower alkoxy or lower alkoxycarbonyl.

2. A naphtholactam of claim 1, wherein X is —NH— or oxygen.

3. A naphtholactam of claim 1, wherein W is ethylene or phenylene.

4. A naphtholactam of claim 1, of the formula

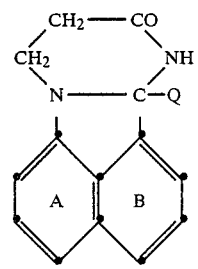

wherein Q is a substituted phenyl radical of the formula

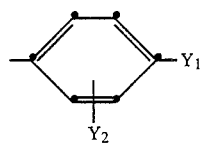

a 3-indolyl radical of the formula

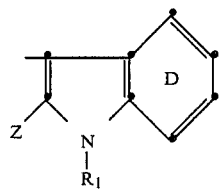

a 3-carbazolyl radical of the formula

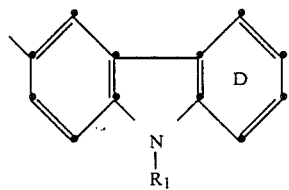

a 3-indolinyl radical of the formula

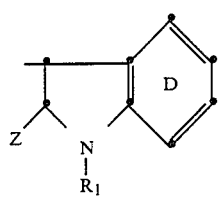

a tetrahydroquinolinyl radical of the formula

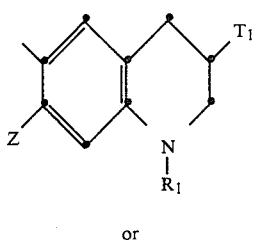

or

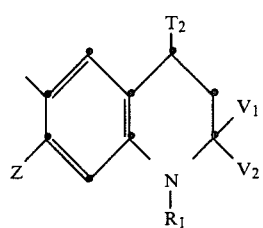

or a benzomorpholino radical of the formula

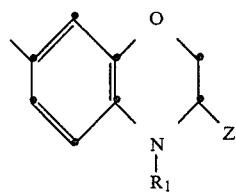

$Y_1$ is $-OZ_1$ or

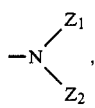

$Y_2$ is hydrogen, halogen, nitro, lower alkyl or lower alkoxy,

Z is hydrogen, lower alkyl or phenyl, $Z_1$ and $Z_2$, each independently of the other, are hydrogen, $C_1-C_{12}$ alkyl which is unsubstituted or substituted by halogen, hydroxyl or lower alkoxy, or are cycloalkyl, phenyl, benzyl, or phenyl or benzyl each substituted by halogen, nitro, cyano, lower alkyl, lower alkoxy or lower alkoxycarbonyl, or $Z_1$ and $Z_2$, together with the nitrogen atom to which they are attached, are a 5- or 6-membered saturated heterocyclic radical, $R_1$ is hydrogen, $C_1-C_{12}$ alkyl which is unsubstituted or substituted by halogen, hydroxyl or lower alkoxy, or is benzyl or benzyl which is substituted by halogen, nitro, lower alkyl or lower alkoxy, $T_1$ and $T_2$, each independently of the other, are hydrogen, halogen, hydroxy, lower alkyl or lower alkoxy, $V_1$ and $V_2$, each independently of the other, are hydrogen, lower alkyl, cycloalkyl or benzyl, or both taken together are alkylene; and the rings A, B and D, each independently of one another, are unsubstituted or substituted by halogen, nitro, cyano, lower alkyl, lower alkoxy or lower alkoxycarbonyl.

5. A naphtholactam according to claim 4, wherein Q is a substituted phenyl radical of the formula (2a) or a tetrahydroquinolinyl radical of the formula (2f).

6. A naphtholactam according to claim 5, of the formula

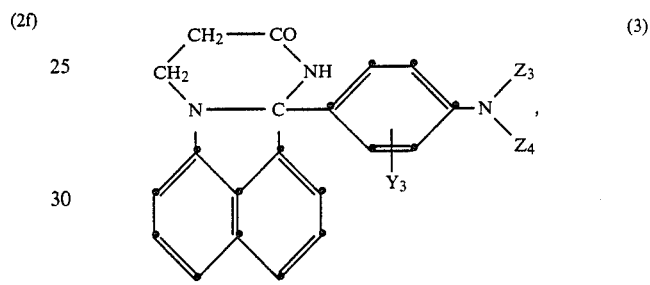

wherein $Z_3$ is lower alkyl, phenyl, lower alkylphenyl, lower alkoxyphenyl or benzyl, $Z_4$ is lower alkyl, phenyl or benzyl, and $Y_3$ is hydrogen, halogen, methyl, methoxy or ethoxy.

7. The naphtholactam of the formula (3) according to claim 6, wherein $Z_3$ and $Z_4$, each independently of the other, are lower alkyl or benzyl and $Y_3$ is hydrogen or methoxy.

8. A naphtholactam according to claim 5, of the formula

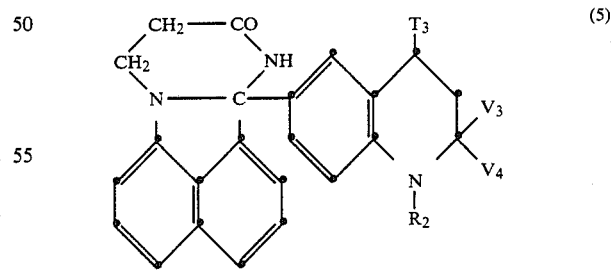

wherein each of $T_3$, $V_3$ and $V_4$ is lower alkyl and $R_2$ is $C_1-C_8$-alkyl or benzyl.

9. The naphtholactam of the formula (5) according to claim 8, wherein $T_3$, $V_3$ and $V_4$ are each methyl and $R_2$ is ethyl.

10. A naphtholactam of claim 1, of the formula (4)
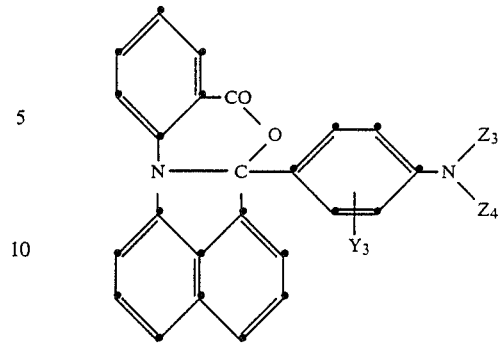
wherein $Z_3$ is lower alkyl, phenyl, lower alkylphenyl, lower alkoxyphenyl or benzyl, $Z_4$ is lower alkyl, phenyl or benzyl, and $Y_3$ is hydrogen, halogen, methyl, methoxy or ethoxy.
* * * * *